United States Patent [19]

Koreska et al.

[11] Patent Number: 4,784,506
[45] Date of Patent: Nov. 15, 1988

[54] BREAKABLE AMPULE WITH SWAB

[75] Inventors: Robert Koreska, Paris; André DeSaint-Leon, Meaux, both of, France

[73] Assignee: Kores Holding Zug AB, Zug, Switzerland

[21] Appl. No.: 26,708

[22] PCT Filed: Jul. 8, 1986

[86] PCT No.: PCT/FR86/00244

§ 371 Date: May 18, 1987

§ 102(e) Date: May 18, 1987

[87] PCT Pub. No.: WO87/00487

PCT Pub. Date: Jan. 29, 1987

[30] Foreign Application Priority Data

Jul. 17, 1985 [FR] France .............. 85 10939

[51] Int. Cl.⁴ .............. A47L 25/00; A47L 17/00; A61M 35/00
[52] U.S. Cl. .............. 401/132; 401/133; 401/134; 401/196; 604/3
[58] Field of Search .............. 401/57, 92, 132, 133, 401/134, 196; 604/3

[56] References Cited

U.S. PATENT DOCUMENTS

| | | | |
|---|---|---|---|
| 194,886 | 9/1877 | Bartram ..................... | 401/92 |
| 3,152,352 | 10/1964 | Kosik, Sr. .................. | 401/132 |
| 3,774,609 | 11/1973 | Schwartzman ............ | 401/134 X |
| 3,790,291 | 2/1974 | Hung et al. ................ | 401/57 |
| 3,924,623 | 12/1975 | Avery ........................ | 604/3 |
| 4,563,103 | 1/1986 | Van Overloop et al. ... | 401/134 |

FOREIGN PATENT DOCUMENTS

| | | | |
|---|---|---|---|
| 55924 | 2/1939 | Denmark ................... | 401/133 |
| 517878 | 5/1929 | Fed. Rep. of Germany | 401/133 |
| 153904 | 7/1938 | Fed. Rep. of Germany | 401/133 |
| 670101 | 1/1939 | Fed. Rep. of Germany | 401/133 |
| 2214709 | 2/1973 | Fed. Rep. of Germany | 401/132 |
| 6827 | 6/1893 | Switzerland .............. | 401/92 |

Primary Examiner—Steven A. Bratlie
Attorney, Agent, or Firm—Sughrue, Mion, Zinn, Macpeak, and Seas

[57] ABSTRACT

A device for applying a predetermined quantity of liquid to a surface, the liquid being contained in a breakable ampule which is substantially cylindrical and enclosed in a flexible and resistant casing closed at one end with an absorbent material, wherein the device comprises a tubular body open at one end, accommodating the ampule and comprising at least two flexible blades formed in its wall, placed substantially opposite each other, each of these blades having at least one tappet facing inward and offset longitudinally with respect to the corresponding tappet of the other blade.

5 Claims, 2 Drawing Sheets

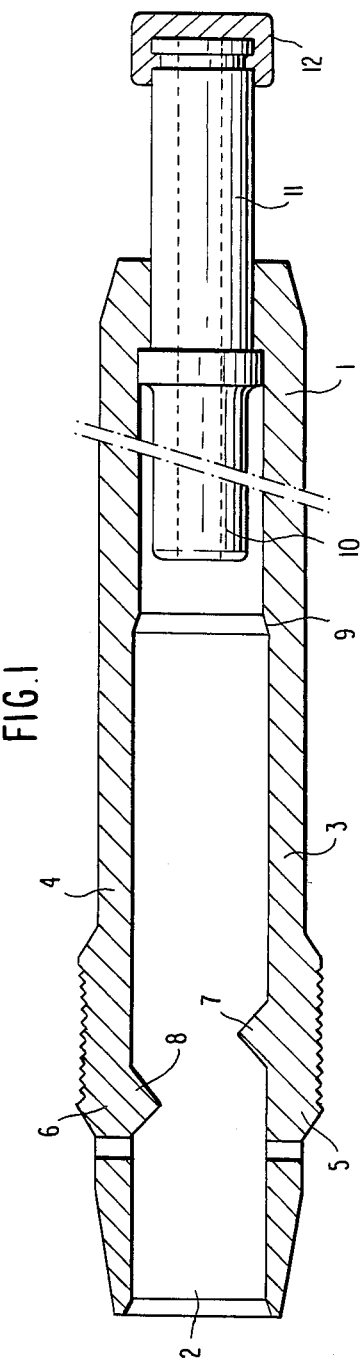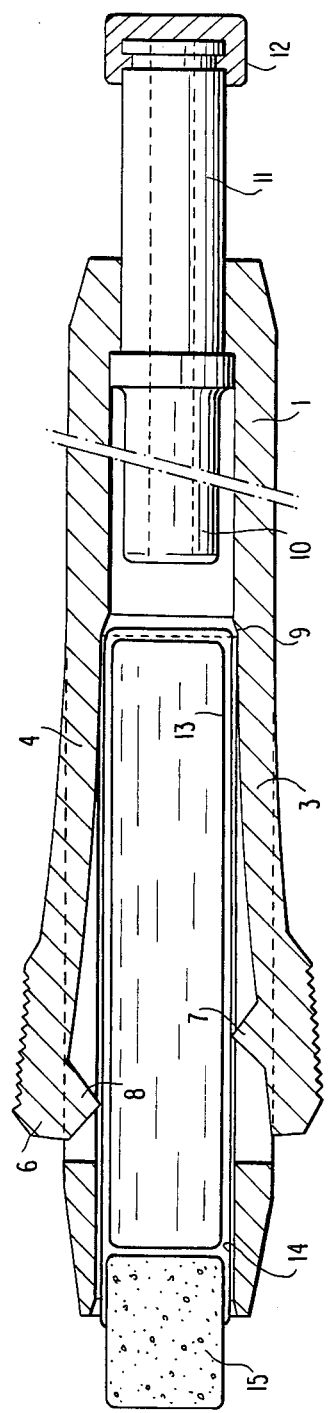

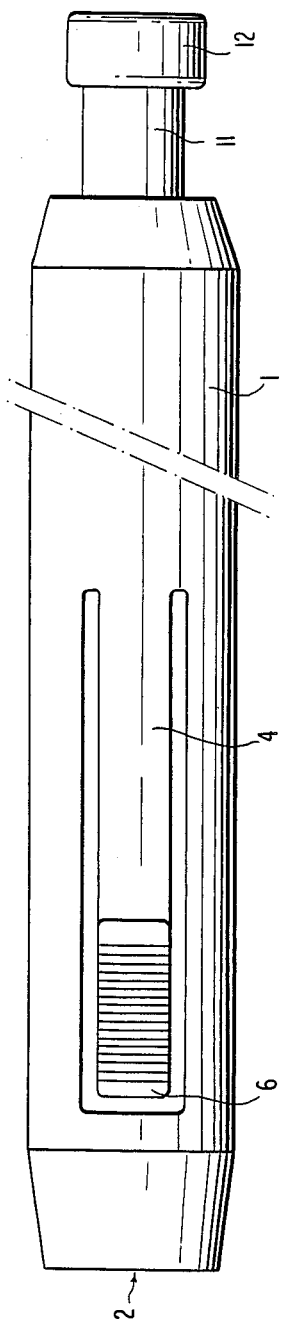

BREAKABLE AMPULE WITH SWAB

This invention pertains to a device for applying a fluid to a surface and more specifically, to a device making it possible to apply a predetermined quantity of a liquid to a surface by coating.

When one wishes to manually apply a relatively limited amount of liquid on to a surface, for example, a few millimeters of a solvent, liquid glue or a varnish, the most simple method consists of using a brush-type applicator which is dipped into the liquid to be applied and is next passed over the surface to be coated or cleaned so that a film of liquid may be placed thereon.

This method involves the use of a container holding a relatively large quantity of liquid and involves considerable loss of liquid and an irregular application.

To make it possible to apply a predetermined amount of liquid, it has been proposed to use single doses, for example, in the form of a breakable ampule or a breakable capsule containing a specific quantity of liquid, which is broken in order to spread the liquid on an absorbent surface or a brush, so that it can be spread over the surface. However, breaking the ampule or capsule containing the liquid is often difficult; it does not always occur at the desired location, and the user can be injured by contact with debris from the ampule or the liquid released.

British Pat. No. 2,001,285 describes a device for applying a liquid glue, comprising a plunger making it possible to pierce and compress a cartridge to cause the glue to issue through an opening blocked by a ball. In U.S. Pat. No. 4,389,132, the liquid to be applied is also contained in a plastic cartridge pierced by a tube. These known devices, however, are relatively complex and do not prevent the applicator by which the liquid on the surface is to be coated from becoming soiled.

The object of this invention is a device which is simple, inexpensive to produce and, which makes it possible to easily and safely apply a predetermined amount of a liquid contained in a breakable ampule or breakable capsule by coating.

The device according to this invention is the type which comprises a dose of liquid in a breakable ampule or breakable capsule, and has a tubular body which is open at one end accommodating a breakable ampule or breakable capsule which is essentially cylindrical and enclosed in a flexible, resistant casing, and having in its wall at least two flexible blades placed essentially opposite each other, with each of these blades having at least one tappet directed towards the inside and offset longitudinally with respect to the corresponding tappet of the other blade.

The flexible blades can advantageously be made by a simple cutout in the tubular body.

The breakable capsule or breakable ampule preferably is in the shape of a cylinder, extended so that it can be introduced into the tubular body through its open end. It is enclosed in a casing made of flexible and resistant material, of the same essentially cylindrical shape, closed at one end with an absorbent material acting as an applicator wick or pad, which extends outside of the tubular body when the ampule or the capsule is placed therein.

At its end opposite the opening, the tubular body preferably has a pusher, comprised for example of a plunger, which can slide freely along the longitudinal axis. This pusher is forced back when the capsule or ampule is placed in the tubular body, so that a shaft connected to the pusher protrudes from the tubular body, at its end opposite the opening. This shaft can next be activated to force back the pusher and eject the capsule or ampule from the tubular body, after which the device according to the invention is used.

When the capsule or ampule is placed in the tubular body, it forces the tappets and the flexible blades to which they are attached outward. By exerting pressure on the blades, the tappets, which are pointed and are offset longitudinally with respect to each other, exert a shearing effect which causes the ampule to break through the casing, and prevent the casing from sliding outside of the tubular body. The liquid in the ampule is thus placed in direct contact with the absorbent material extending outside of the tubular body.

The device according to the invention, which is comprised of the tubular body and the casing housing the broken ampule, can then be used as an applicator brush or pad to place a film of liquid on the surface to be treated. During this operation in which the ampule is broken and the liquid is applied, the user holds the device by the tubular body, which prevents any risk of injury or contamination from debris from the ampule or the liquid it contains. In addition, when use is completed, it is sufficient to act on the shaft of the pusher to eject the ampule and its casing without contact with the fingers.

The ampule is preferably made of glass which is resistant to the liquid it contains. The casing can be made of any flexible material resistant enough so that it does not tear under the action of the tappets. Polyethylene, for example, can be used.

The tubular body can be made of a light metal, an alloy or plastic material such as polypropylene, nylon, polystyrene, etc. It can be advantageous to use a nylon reinforced with glass fibers for the tubular body, and a harder material, such as polypropylene, for the pusher.

The device according to the invention can be used to apply a liquid to a surface, especially to clean typewriter character using a solvent such as an alcohol or trichloroethylene. It can also be used to apply a protective varnish to a surface. Of course, the applicator can be modified freely depending on the liquid used and the conditions under which the device is implemented.

The characteristics and advantages of the invention will emerge in greater detail in the description below of a non-limitative embodiment, with reference to the attached drawings, which show the following:

FIG. 1: a longitudinal cross section of a device broken down according to this invention.

FIG. 2: a longitudinal cross section of the device in FIG. 1, housing an ampule of liquid in its casing, ready to be used.

FIG. 3: a top view of the device in FIG. 1.

As shown in FIG. 1, the device comprises a tubular body (1) which is essentially cylindrical, open at one end (2). Two flexible blades (3) and (4) are cut out of this cylindrical body (1), with the ends (5) and (6) of the former respectively being free, and each respectively holding a pointed tappet (7) and (8) molded in the blade material.

The inside of the tubular body (1) has an annular collar (9) which serves to center and hold the casing enclosing the ampule, which is introduced through the opening (2).

At its end opposite the ampule (2), the tubular body (1) comprises a pusher (10) in the form of a plunger which slides freely along the longitudinal axis of the tubular body, and whose shaft (11) passes through the body (1) at its end. The shaft (11) is topped with a cap (12) which facilitates its action and prevents it from passing out of the body (1).

When the ampule is placed in the tubular body (1) through its opening (2), as shown in FIG. 2, it forces back the tpapets (7) and (8) and the blades (3) and (4) which hold them; its centering is ensured by the collar (9), the position which is provided depends on the size of the ampule and its casing and, in the extreme position, it can come to stop against the pusher (10). Depending on its size and shape, the ampule is in contact with the pusher (10); under the normal conditions for use, it is nonetheless sufficient for it to be held by the collar (9). The glass ampule (13) is enclosed in a flexible and resistant casing (14); its end which extends through the opening (2) is closed by an absorbent applicator (15) pad.

Pressure on the two blades (3) and (4), formed by cutout in the tubular body (1) as shown in FIG. 3, causes a shearing effect on the ampule (13) through its casing (14) because of the longitudinally offset position of the tappets (7) and (8) with respect to each other. The liquid contained in the ampule (13) is then released inside the flexible casing (14) and comes into contact with the absorbent pad (15) which thus becomes saturated. After use, by acting on the cap (12), the shaft (11) and the pusher (10) are forced back and the broken ampule (13), its casing (14) and the pad (15) are removed.

We claim:

1. A device for applying a predetermined quantity of a liquid to a surface, said liquid being contained in a breakable ampule (13) which is substantially cylindrical and enclosed in a flexible and resistant casing closed at one end with an absorbent material, wherein said device comprises a tubular body (1) open at one end (2), accommodating the ampule (13) and comprising at least two flexible blades (3) and (4) formed in its wall, placed substantially opposite each other, each of these blades having at least one tappet (7) and (8) facing inward and offset longitudinally with respect to the corresponding tappet of the other blade.

2. A device according to claim 1, characterized in that the flexible blades comprise cutouts in the tubular body.

3. A device according to claim 1, characterized in that the ampule (13) or breakable capsule is contained in a flexible and resistent casing (14) which is closed at one end by an absorbent material (15) which extends outside of the tubular body (1) when the breakable ampule (13) or the breakable capsule is placed therein.

4. A device according to claim 1, characterized in that it comprises, at its end opposite the opening, a pusher (10) connected to a shaft (11) protruding outside of the tubular body (1).

5. A device according to claim 1, characterized in that the tubular body (1) has on its internal wall an annular collar (9) which makes it possible to center and hold the casing (14).

* * * * *